United States Patent [19]

Smith

[11] 4,145,680
[45] Mar. 20, 1979

[54] ACOUSTIC IMAGING SYSTEM

[75] Inventor: Richard W. Smith, Richland, Wash.

[73] Assignee: The United States of America as represented by the United States Department of Energy, Washington, D.C.

[21] Appl. No.: 843,182

[22] Filed: Oct. 18, 1977

[51] Int. Cl.$^2$ ............................ G01S 9/66; G01S 7/62
[52] U.S. Cl. ................................. 340/5 MP; 340/1 R; 73/626; 73/628
[58] Field of Search ............ 340/5 MP, 5 H, 85, 1 R; 73/619, 620, 626, 628, 633, 641

[56] References Cited

U.S. PATENT DOCUMENTS 3,792,423   2/1974   Becker et al. ..................... 340/5 MP

*Primary Examiner*—Richard A. Farley

*Attorney, Agent, or Firm*—Dean E. Carlson; Richard E. Constant

[57] ABSTRACT

An acoustic imaging system for displaying an object viewed by a moving array of transducers as the array is pivoted about a fixed point within a given plane. A plurality of transducers are fixedly positioned and equally spaced within a laterally extending array and operatively directed to transmit and receive acoustic signals along substantially parallel transmission paths. The transducers are sequentially activated along the array to transmit and receive acoustic signals according to a preestablished sequence. Means are provided for generating output voltages for each reception of an acoustic signal, corresponding to the coordinate position of the object viewed as the array is pivoted. Receptions from each of the transducers are presented on the same display at coordinates corresponding to the actual position of the object viewed to form a plane view of the object scanned.

7 Claims, 7 Drawing Figures

ACOUSTIC IMAGING SYSTEM

BACKGROUND OF THE INVENTION

The invention described herein was made in the course of, or under, a contract with the United States Energy Research and Development Administration, and pertains generally to imaging systems, and more particularly to acoustic imaging systems.

To date, various techniques have been used in the electronic art for imaging viewed objects. For example, both two dimensional and three dimensional display systems have been developed. Where three dimension imaging systems have been employed, dual cathode ray tube displays have been generally utilized, i.e. sonar display systems. In the area of detecting and mapping objects in opaque liquids, as well as nondestructive testing of objects for internal flaws, ultrasonic imaging, which typically utilizes either a B- or C- scan two dimensional display system, has found widespread usage. In the C-scan technique, a short ultrasonic pulse is transmitted by a transducer in the direction of an object which is to be imaged. The reflected signals from the surfaces of the object and/or internal flaws are then detected by the same transducer and amplified and time gated to include only those areas of the object to be imaged. The detected signal is recorded as a single point on a recording device which is scanned in synchronization with the transducer. The B-scan technique is similar except that time or depth information from a single cross-section is displayed on the face of a cathode ray tube. In the case of both the B- and C- scan techniques, the resulting image is a flat pattern of the viewed object. Hence, both these excellent analytical tools suffer a basic shortcoming in the fact that both spatial and depth information cannot be displayed on a single record. Thus, only a very narrow perspective of the viewed object can be established. Accordingly, in specialized areas, requiring for example the evaluation of the true nature of an unknown object, these techniques leave much to be desired.

The discovery of holography, both optical and ultrasonic, for imaging viewed objects has afforded basic improvements over the earlier developed ultrasonic B- and C- scan techniques. With ultrasonic holography both spatial and depth information are recorded simultaneously, but ultrasonic holography does not, however, produce a three dimensional image as is in fact produced in optical holography due to the difference in wavelength between the ultrasound and the laser light used in the reconstruction of the hologram.

U.S. Pat. No. 3,792,423 substantially contributed to the art by providing a mechanism for displaying an isometric image of an acoustically viewed object. However, even this improvement fails to define surfaces other than those perpendicular to an overhead line of projection of the acoustic signal.

Without the ability to view a given point on an object from several perspectives, it is difficult, if not impossible to truly reconstruct the object into a recognizable format in an acoustically viewed system. Accordingly, an improved acoustic imaging system is desired that can view the same coordinates of an object from several perspectives and display the information in an easily interpretable format.

SUMMARY OF THE INVENTION

Briefly, this invention overcomes the deficiencies of the prior art by providing apparatus operable to present an acoustic reception from a particular location at the same position on a display regardless of which of a number of transducers views the location or the perspective from which the location is viewed.

To this end, this invention provides a laterally extending array of a plurality of acoustic transducers respectively spaced at a known distance from a given point and directed to transmit and receive acoustic signals along preestablished transmission paths substantially parallel to a preselected plane. The array is operable to pivot within the preselected plane about the given point. Means are provided for generating output voltages in response to an acoustic reception which correspond to the coordinate position of the object viewed as the array is pivoted. The receptions from the respective transducers are then presented on the same display at coordinate positions corresponding to the actual viewed locations.

BRIEF DESCRIPTION OF THE DRAWINGS

For a better understanding of the invention, reference may be had to the preferred embodiment, exemplary of the invention, shown in the accompanying drawings, in which.

DESCRIPTION OF THE PREFERRED EMBODIMENT

Figure 1:
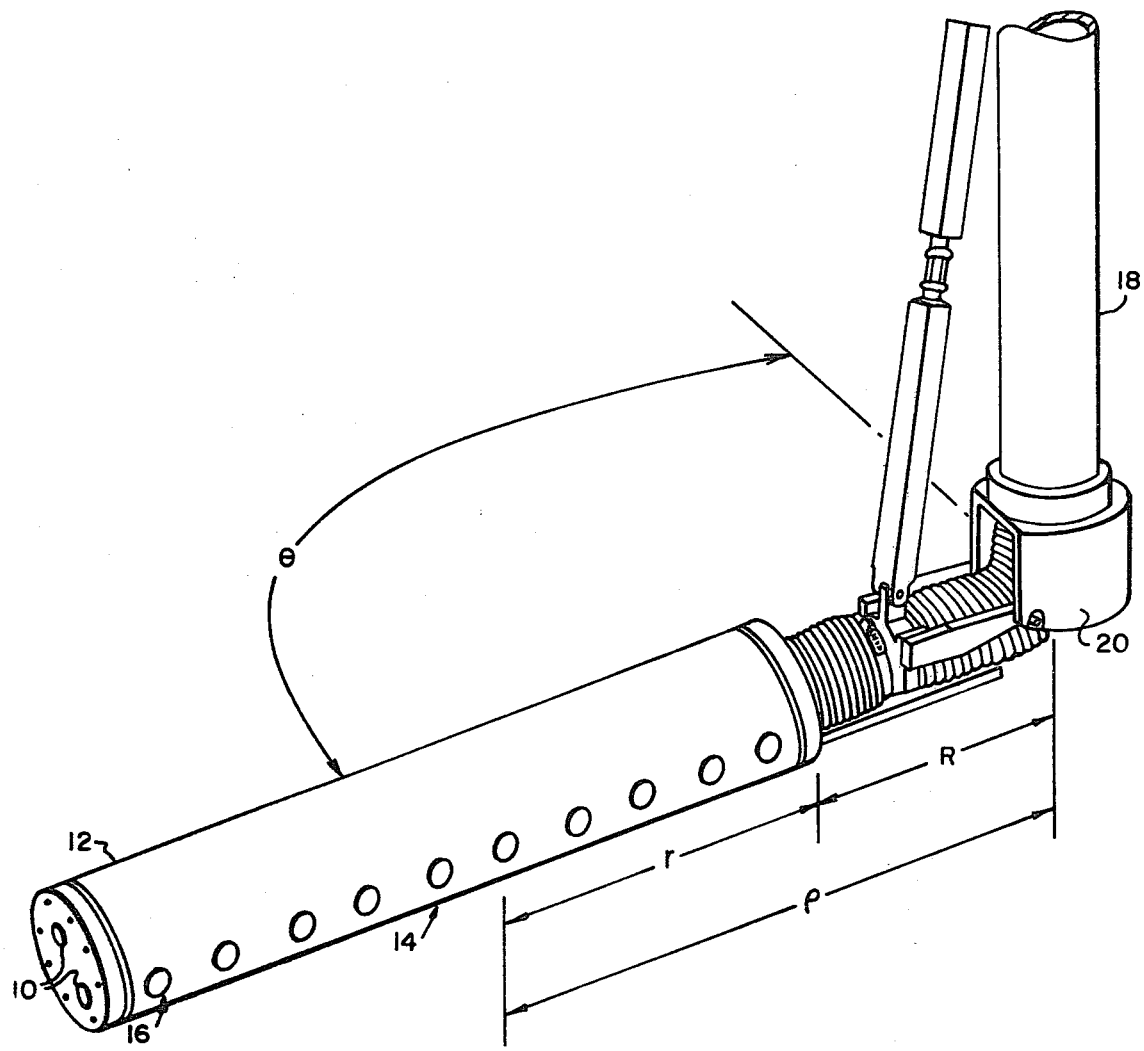
FIG. 1 is a perspective view of a transducer array and pivoting arm arranged in accordance with this invention.

The isometric imaging system described in U.S. Pat. No. 3,792,423 was devised to meet the inspection requirements of liquid metal fast breeder nuclear reactors. The system was developed as an alternative to costly visual inspection methods which would require interrupting power reactor electrical generation to drain the optically opaque liquid sodium coolant so that visual inspection means could be employed. This system was developed to locate, identify and form images of in-vessel components during reactor shutdown and refueling.

As contemplated, the inspection system of U.S. Pat. No. 3,792,423 is comprised of three subsystems (generally illustrated in FIG. 1): an end ranging subsystem that measures and displays in digital form the distance from transducer 10, located on the end of the scanning arm 12, to the nearest normal surface; an imaging subsystem 14 that uses acoustic time of flight information from eleven transducers outwardly extending from the bottom of the scanning arm 12 to generate high resolution images; and a side ranging subsystem 16. The principal function of the side ranging transducers 16 originally was to provide the operator of the viewing system with ultrasonic data from the side of the scanning arm. The side ranging data enabled the operator to locate internal reactor obstructions that could block movement of the scanning arm. The side ranging system contemplated by the afore-cited patent presented an A-scan of the information developed (time vs. echo amplitude) from the twelve side ranging transducers, all operating simultaneously and synchronously, on a single oscilloscope trace. The respective transducer receptions (as chosen by the operator) could also be individually displayed on a separate oscilloscope trace. This type of system requires a great deal of time consuming interpretation by the operator to identify any obstruction that is located. Its principal value would be in warning of an imminent collision of the scanner arm with an obstructing object.

This invention provides an improvement which presents all the data from the side ranging transducers, as they are translated through an angle $\theta$, as a map or plan view of the reactor components providing a presentation that can be readily interpreted. To accomplish this end, the effects of the scanner arm position and which transducer detected the object are eliminated from the presentation so that an echo from an object is displayed at the position corresponding to the location of the object in the reactor.

In accordance with this invention in the course of a normal scan, when the scanner arm 12 is perpendicular to the vertical support shaft 18, a surface or object within the field of scan will be typically viewed over a wide range of angles by many of the transducers 16 of the side ranging system. Thus, the probability of detecting a surface within the field of view is high, and a surface detected is more clearly defined.

A further extension of the system of this invention is the generation of a three dimensional image obtained by raising the scanner arm 12 vertically in increments while sweeping in the $\theta$ direction. This would generate a number of images at different levels. Utilizing an isometric projector as defined in U.S. Pat. No. 3,792,423, a three dimensional image capable of being rotated and tilted electronically can be displayed. Alternatively, a three dimensional image can be generated from additional information obtained from a scan effected with the scanner arm 12 placed in a vertical position parallel to the support shaft 18.

The system of this invention operates by measuring the distance to a reflecting object or surface and printing a dot by unblanking the display scope at the point on the display which corresponds to the location of the reflecting object. This is accomplished regardless of the position of the scanner arm 12 or even which transducer 16 viewed the object. The exemplary system to be described in this embodiment employs ten equally spaced transducers 16 along each side of the scanning arm 12 and one end ranging transducer 10. To avoid interference, the transducers 10 and 16 are pulsed and interrogated individually and sequentially.

Figure 2:
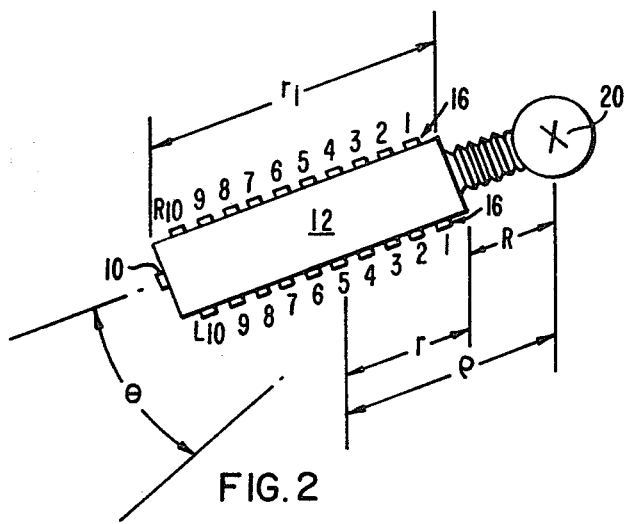
FIG. 2 is a top schematic view of the transducer array of FIG. 1.

As illustrated in FIG. 2, the transducers 16 employed in the side viewing system of this invention are uniformly spaced along both sides of the scanning arm and view outwardly perpendicular to the axis of the scanner arm 12. One of the end ranging transducers 10, which looks parallel to the axis of the scanner arm at the end of the arm, is incorporated within the system to provide a full field of view. As the arm 12 sweeps through some angle $\theta$, a reflecting object is viewed typically over a wide range of angles by a number of transducers. This provides redundancy, and an entire image can generally be obtained in a single sweep of the scanning arm. Furthermore, because the transducers must view a reflecting surface normally in order to see or detect its presence, the angular excursion of the transducers as the scanner arm 12 is pivoted makes detecting an object much more likely.

The processing electronics of this invention include an analog circuit that generates the signal voltages which are applied to the X and Y axes of a display storage oscilloscope to position an echo from any transducer at the correct location on the screen; that is, the position that corresponds to the location of the reflecting object in the reactor. The analog circuit is thus very basic to the operation of the invention and can be better appreciated following an understanding of the relative geometry of the system.

A top view of the scanner arm of FIG. 1 is illustrated in FIG. 2. The arm is shown deflected $\theta$ degrees in the $\theta$ direction and a distance R in the $\rho$ direction. The total distance $\rho$ to a particular transducer, i.e., $R_5$, is the sum of the distances R and r. Both $\theta$ and R are variable and are measured by position sensors. A signal corresponding to the distance r is internally-generated and is proportional to the distance from the end of the arm to a particular transducer. If, for example, transducer $R_5$ is being interrogated, then a signal r is generated that is proportional and corresponds to the distance from the end of the arm to transducer $R_5$. In this manner, this invention uniquely specifies the location and orientation of each transducer.

Figure 3:
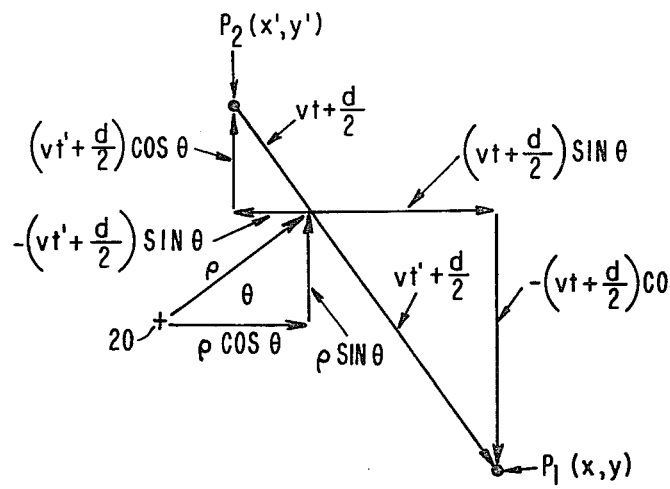
FIG. 3 is a diagrammatic representation of the side ranging geometry of the transducers illustrated in FIG. 2.

Now the distance vt to an object viewed by a particular transducer is determined by measuring the time of flight of an acoustic pulse reflected off the object and back to the transducer. FIG. 3 illustrates the geometry for the transducers extending in a lateral array along the side of the scanner arm 12. The distance vt to a point $P_1$ (XY) in a particular direction from the scanner arm is measured for example by transducer $R_5$ and, assuming point 20 as the pivot of the scanner arm 12 is given in cartesian coordinates by:

$$X = \rho \cos\theta + (vt + (d/2)) \sin \theta,$$
$$Y = \rho \sin\theta - (vt + (d/2)) \cos \theta, \qquad (1)$$

where d is the diameter of the scanner arm. Signal voltages proportional to these quantities applied to the horizontal and vertical axes of a storage oscilloscope will deflect the electron beam to a point on the screen $P_1$ corresponding to the actual location of the object. At $P_1$, the previously blanked oscilloscope is unblanked for a short period to print the dot. For a transducer on the opposite side of the scanner arm (for example $L_5$) the position of a reflector at point $P_2$ (X'Y') is given by the equations:

ti $X' = \rho \cos\theta - (vt' + (d/2)) \sin \theta,$ $$Y' = \rho \sin\theta + (vt' + (d/2)) \cos \theta. \qquad (2)$$

Note that Equations (1) differ from Equations (2) only in that signs of the second terms (the ramp plus offset) are reversed.

Figure 4:
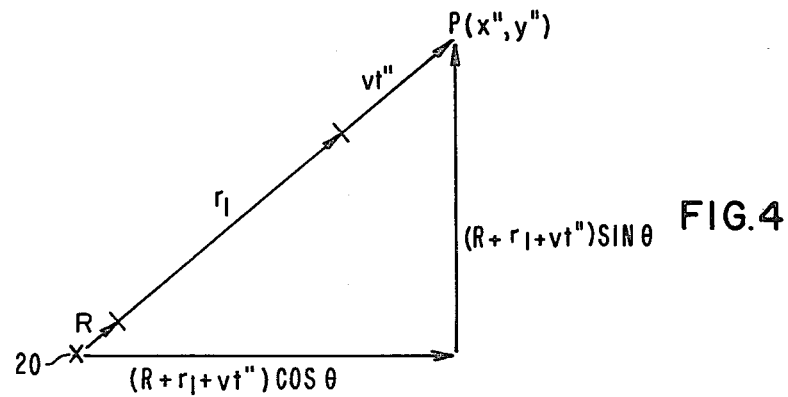
FIG. 4 is a diagrammatic illustration of the end ranging geometry of the transducers illustrated in FIG. 2.

For an end transducer (centered on and looking off the end of the scanner arm 12 as shown schematically by reference character 10 in FIG. 2, and geometrically in FIG. 4) the position of a reflector at $P_3$ ($X''Y''$) is given by:

$$X'' = (r_1 + R + vt'') \cos \theta,$$

$$Y'' = (r_1 + R + vt'') \sin \theta. \quad (3)$$

Here $r_1$ is the distance from the end of the scanner arm to the end transducer. In the above equations, the quantities $vt$, $vt'$ and $vt''$ are the distances to points P, $P_1$, and $P_2$, respectively, as determined by measuring the time of flight of an acoustic pulse. The constant v is one-half the velocity of propagation of ultrasound in the medium of travel, in this example sodium, while t, t' and t'' are the times of flight of the respective signals. For the system of this invention, the quantity vt is represented by a ramp signal of slope v that is generated by a digital clock and has a step increment equivalent to 0.1 inch in this example. In practice, the ramp, started when a transducer is pulsed, moves the oscilloscope beam away from the scanner arm at a rate corresponding to the time of flight of the pulse. When an echo is received, the oscilloscope is unblanked momentarily at the point which corresponds to the echo location. A storage-type oscilloscope will store the echo on the screen and can maintain the image substantially for the time of scan.

The net result of Equations (1) through (3) is that considerations of the position of the scanner arm, and even which transducer sees the reflection is eliminated from the presentation, because a particular location on the oscilloscope display screen can be uniquely associated with the corresponding location in the scanning field. This means that scanning the transducer arm through a large angle $\theta$ while the transducers are pulsed and interrogated at a rapid rate will result in an object typically being viewed by a number of transducers over a large angle. A high degree of redundancy is thus provided, and any surface which the transducers view normally over the path of the scan will be detected.

Operation of the scanner when the arm 12 is vertically oriented to obtain a three dimensional image can be represented by Equations (1), (2) and (3) by eliminating the terms that represent deflections along the arm. The corresponding equations are then reduced to:

$$X = (vt + (d/2)) \sin \theta$$
$$Y = -(vt + (d/2)) \cos \theta \quad (1a)$$
$$Z = \rho = r + R,$$

$$X' = -(vt' + (d/2)) \sin \theta$$
$$Y' = (vt' + (d/2)) \cos \theta \quad (2a)$$
$$Z' = r + R,$$

and $$X'' = 0$$
$$Y'' = 0 \quad (3a)$$
$$Z'' = r + R + vt''.$$

The deflections along the arm represented by the deleted terms are perpendicular to the scanning plane of the side transducers. Thus, the equations can be modified as indicated to obtain the third dimension Z necessary for the three dimensional reproduction of the viewed object.

Figure 5:
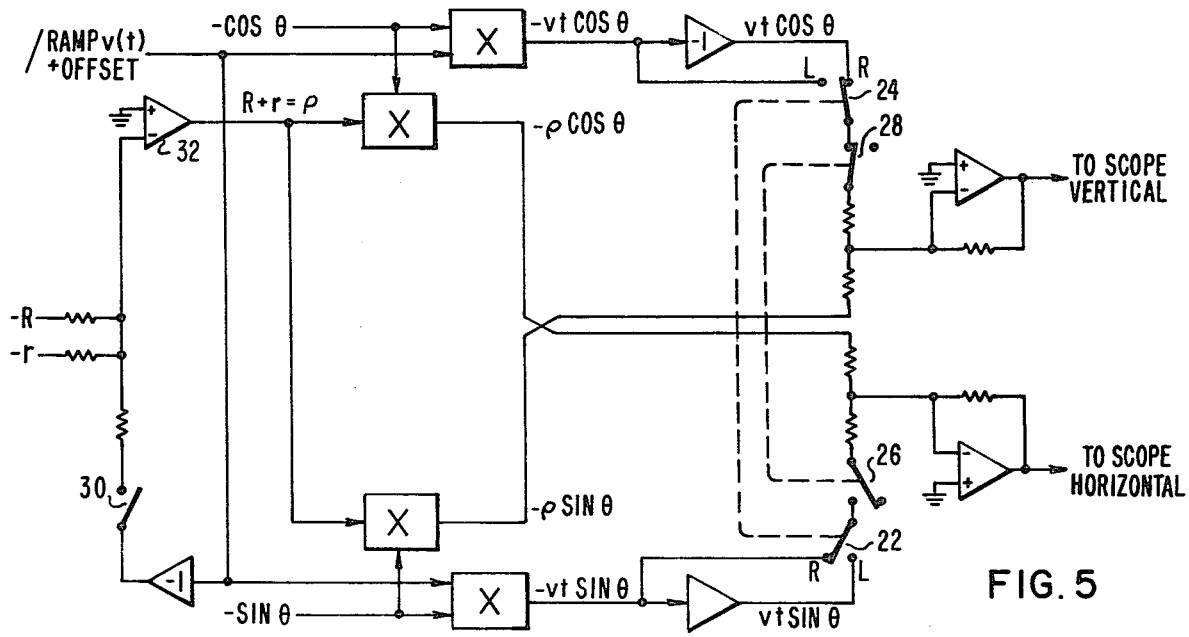
FIG. 5 is a simplified schematic circuitry diagram arranged in accordance with this invention for generating the output voltages corresponding to the coordinate positions of the respective transducer receptions.

FIG. 5 shows a simplified schematic of an electronic system to implement the concept of this invention. When the switches 22, 24, 26, 28 and 30 are in the positions shown, the ramp v deflects the oscilloscope beam to the right of the sanner arm from a point corresponding to the position R + r on the arm. Note that r is a voltage that is proportional to the position of the transducer on the arm. By switching switches 22 and 24 to the L position the ramp deflects the beam to the left of the scanner arm.

To accommodate the end ranging transducer, switches 24 and 28 are opened and 30 is closed, applying the ramp $-v$ to the sum in amplifier 32 and deflecting the oscilloscope beam outward from the position representative of the end of the scanner arm. The switches shown represent fast acting electronic switches which are controlled by external logic which sequentially pulses and interrogates the transducers on the scanning arm. Additional improvements include the ability to display the scanner arm on the scope screen at the operator's discretion, so that the position of the arm with respect to the objects viewed can easily be determined. The angle $\theta$ supplied from a position sensor located on the scanner arm 12 and the reference voltages R and r are provided to correspond with the transducer being interrogated by the switching electronics.

Figure 6:
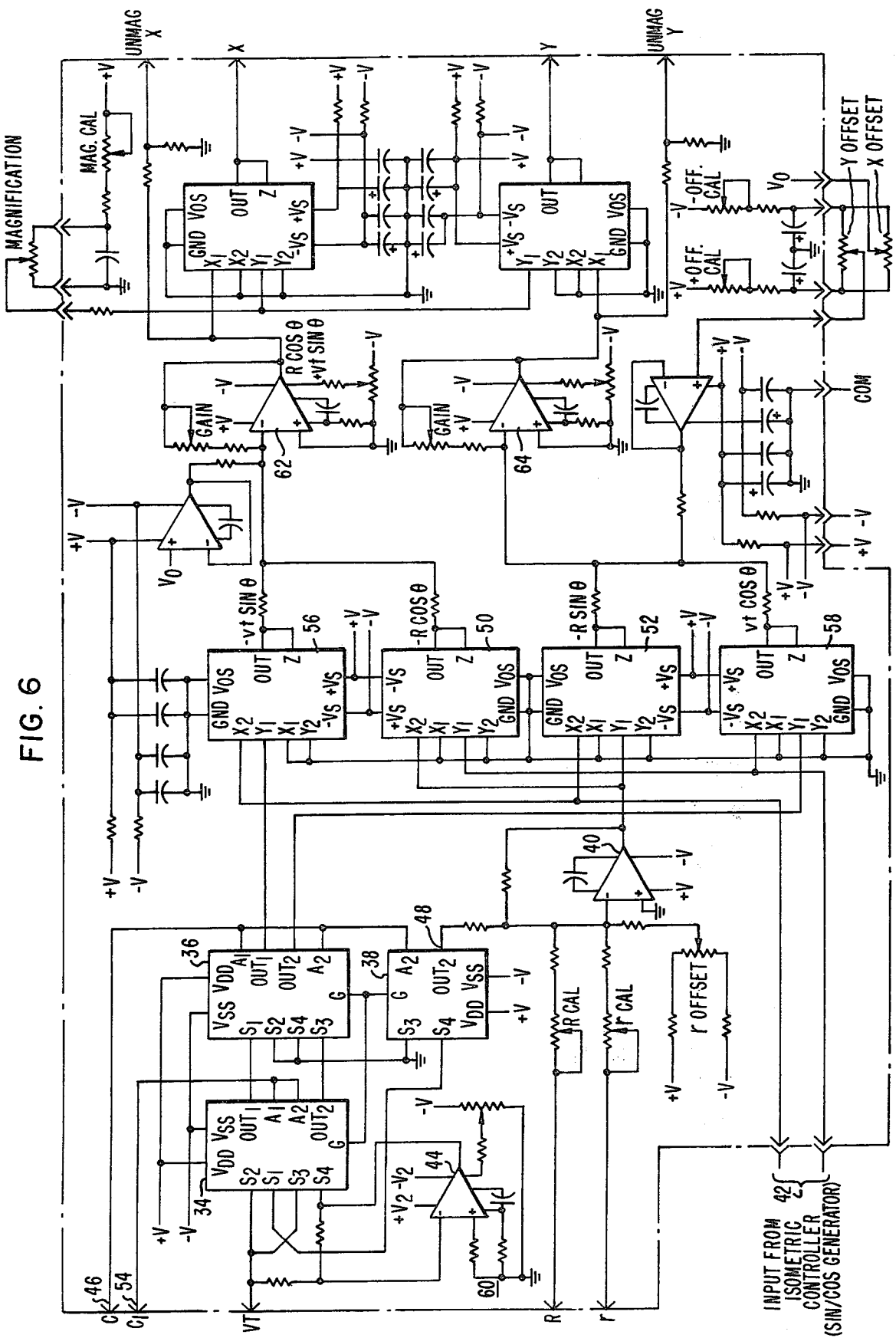
FIG. 6 is a detailed schematic circuitry diagram of the analog controls for processing the transducer outputs in accordance with this invention.

A more detailed circuit illustration is provided in FIG. 6. The electronic switches 34, 36 and 38, controlled by external logic, apply the ramp voltage vt and the required ramp offset voltage to the proper circuit functions at the appropriate time. Signal voltages proportional to $\rho$ are summed in amplifier 40, and voltages proportional to sine $\theta$ and cosine $\theta$ are applied to pins 42 of the circuit board. Amplifier 44 inverts the positive ramp signal vt.

For the purpose of illustration, assuming that a transducer on the side of the scanning arm is to be interrogated, a logical 1 is applied to the 46 input. In this case, pin 48 of switch 38 is shorted to common so the output of amplifier 40 is just $\rho$. The first terms of Equations (1) and (2) are provided at the outputs of multipliers 50 and 52. Now if a transducer on the left side of the arm is to be interrogated, a logical one is applied to input 54, and the second terms of Equation (2) are supplied at the outputs of multipliers 56 and 58. A logical one on input 54 arranges the analog switch 60 to apply a negative ramp $-(vt + d/2)$ to multiplier 56 and a positive ramp $(vt + d/2)$ to multiplier 58. The two terms of Equation (2) which correspond to the X and Y deflection signals are respectively summed in amplifiers 62 and 64 so that the X signal appears at the output 62 and the Y signal appears at the output 64. When the transducer is pulsed, the ramp voltage vt, starting at the offset which corresponds to half the diameter of the scanning arm, deflects the oscilloscope beam to the left of the position on the screen corresponding to the scanning arm, at a rate proportional to half of the velocity of ultrasound in sodium.

For a transducer on the right side of the scanning arm 12, a logical zero is applied to the input 54 which, in effect, reverses the signs of the second terms in Equation (2) by switching the positive ramp (vt + d/2) to multiplier 56 and the negative ramp $-(vt + d/2)$ to multiplier 58. Equations (1) are thus generated and the oscilloscope beam is deflected to the right of the position on the screen corresponding to the scanning arm.

The remainder of the circuit in FIG. 6 is effective to magnify and position the image on the oscilloscope readout. An unmagnified output (UNMAG X and UNMAG Y) is also provided that is not dependent on the setting of the magnifier control.

A simple modification to the analog circuit will establish signals representative of Equations (1a), (2a) and (3a) without requiring a change in inputs. To make this modification, the output of amplifier 40 is disconnected from the inputs of multipliers 50 and 52, and the disconnected inputs are tied to common. With the circuit thus altered the X and Y outputs of the analog circuit will provide signals that correspond to Equations (1a), (2a) and (3a). The quantity Z is obtained from the output of amplifier 40.

To generate a signal representative of Equation (3), which corresponds to the end transducer, input 46 is driven to logical zero. The inputs of multipliers 56 and 58 will then be tied to common and a negative ramp will be applied to the input of the $\rho$ summing amplifier 40. The ramp signal, starting with the proper offset, will then move the oscilloscope beam out from the position that corresponds to the end of the scanning arm at a velocity corresponding to half the velocity of sound in sodium.

Figure 7:
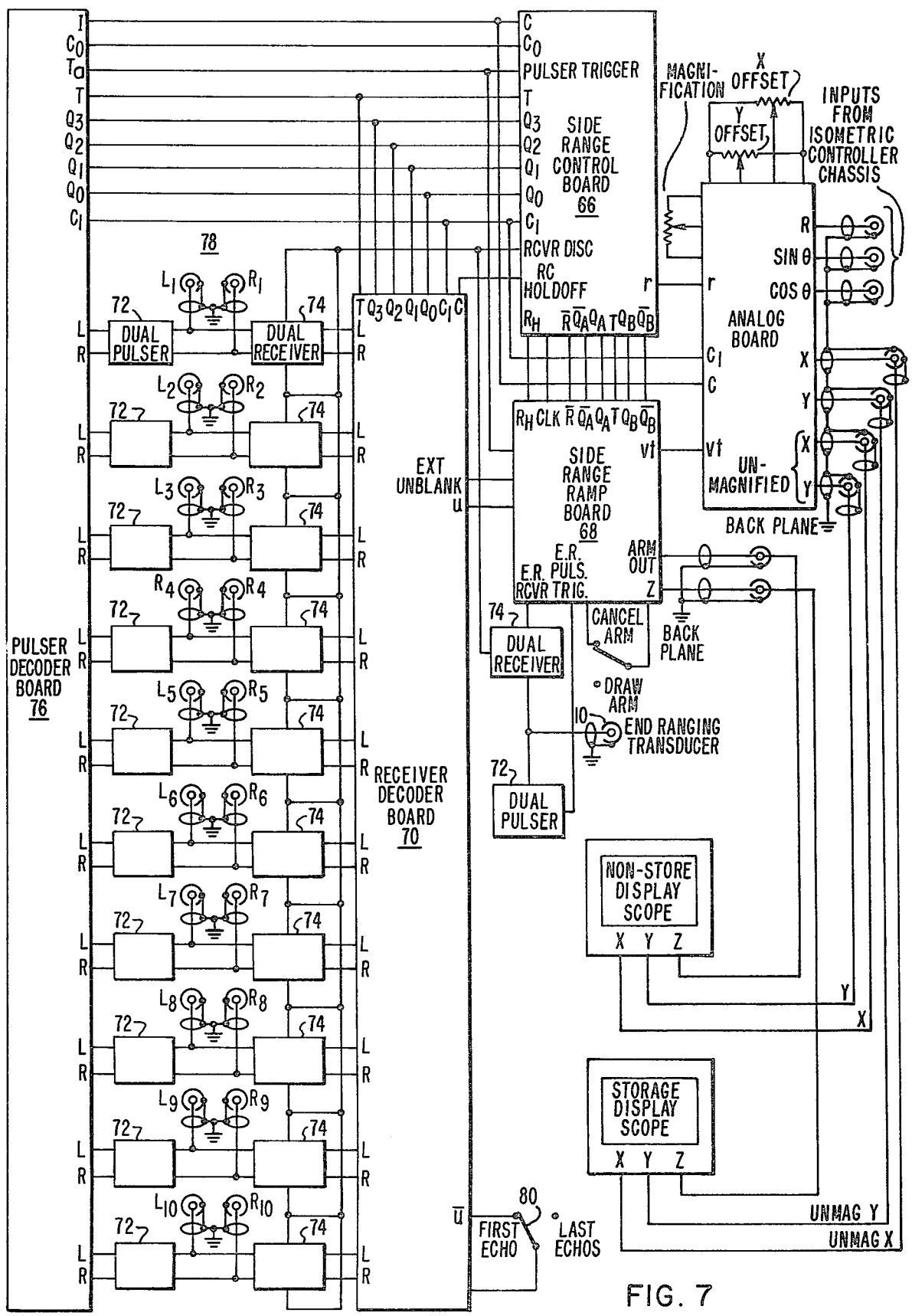
FIG. 7 is an overall block diagram of the processing electronics employed in accordance with one embodiment of this invention.

FIG. 7 illustrates a block diagram of an overall electronics arrangement capable of implementing the exemplary system of this embodiment. The side range control board 66 includes the circuits that generate the signals which control the system. A 9.674 megahertz crystal controlled oscillator generates a clock signal which is divided down to 0.4837 megahertz for the digital ramp register located in the side range ramp circuit arrangement 68. The period of the clock is set to equal the time it takes an acoustic wave to travel 0.1 inch twice in 500° F. sodium. The clock signal is further divided to 0.472 kilohertz to drive registers which multiplex the transducers.

The side ranging transducers are controlled by a binary coded decimal register within the side range control board having outputs $Q_0$, $Q_1$, $Q_2$, $Q_3$, which establishes the transducer location r on the scanner arm. A flip-flop in series with this binary coded decimal register provides a signal $C_1$ which determines whether a transducer on the right or lefthand side of the transducer arm will be interrogated. Thus, starting with location 1 first, the lefthand transducer is interrogated and then the right. The binary coded decimal register then shifts to location 2 where the lefthand and then the righthand transducers are interrogated. This sequence continues until all the side ranging transducers have been interrogated. As the count in the binary coded decimal register accumulates, a digital-to-analog converter operating from this register generates an analog signal r that is proportional to the transducer location on the arm.

At the end of the side range sequence, control is shifted to a binary divide-by-four register $Q_A$, $Q_B$, which interrogates the end ranging transducer, resets the side range register, and "draws" the transducer arm (establishes the transducer arm image on the oscilloscope screen), in that order. When the sequence is completed, control is transferred back to the side range register and the cycle begins again.

The control board generates another signal "T" in synchronization with the clock, which triggers the pulse generators, holds off the receiver inputs for about 40/microseconds, and gradually decreases the discriminator level for the receiver amplifiers. The pulser trigger circuit generates a delayed (approximately 100 nanoseconds with respect to the clock signal) trigger pulse which drives the control registers. This is done to insure that the register has shifted and settled before the trigger pulse is applied to the pulse decoder board 76. The transducers 78 (which include both the transducers 10 and 16) are operated in the pulse/echo mode, where each transducer acts as the transmitter and receiver of acoustic energy. Consequently the receiving circuits have the potential of being exposed to both the transmission and the ringdown of the transducer. To prevent the transmit pulse and the ringdown of the transducers from being communicated to the receiving circuits, the receiver holdoff pulse $R_H$ (approximately 40 microseconds in this example) forces the receivers to disregard any signal received during this period. To further compensate for the transducer ringdown, a discriminator level signal is generated that starts at the end of the $R_H$ pulse and gradually decreases with time. Both the decay rate and the final level of the discriminator signal are adjustable. The discriminator signal is applied to a comparator on the receiver board and all receiver output signals below this discriminator level are disregarded. Thus, the receiver sensitivity is effectively increased with time after the transducer is pulsed, however, weaker signals received from a reflecting object located some distance from the transducer can be disregarded if below the discriminator level. The purpose of the discriminator circuit though in this application is to discriminate against the transducer ringdown and electronic noise. Any real echo, however small, should not be disregarded. Therefore, the discriminator should be adjusted accordingly to the minimum level necessary to compensate for ringdown. Similarly signal "I" is an inhibit input which prevents the side transducer 16 from transmitting while the end units 10 are being used. The "C" output from the Side Range Control Board 66 identifies whether side or end ranging transducers are to be pulsed.

Adjusting the side scan system of this invention for use in other fluids requires only that the plug in crystal oscillator be changed. For example, water requires a clock frequency of 5.837 megahertz. The rate of interrogation of the transducer will be changed, since the operation is synchronous with the clock, but no other adjustments need be made.

The pulse decoder circuit 76 triggers each of the side ranging transducers 78. The $Q_0$, $Q_1$, $Q_2$, $Q_3$, and $C_1$ inputs are decoded to multiplex the input trigger pulse through the proper sequence desired.

The receiver decoder circuit 70 multiplexes the side ranging receiver through the same sequence as the pulse decoder, using the same inputs. After the holdoff period (approximately 40 microseconds) the receiver decoder "listens" to a receiver for about 2 milliseconds (corresponding to a distance of travel of an acoustic signal in sodium of approximately 100 inches). A signal received during this period generates an unblank pulse which turns the oscilloscope display beam on momentarily to impress a dot at the appropriate location corresponding to the echo received. The duration of the unblank pulse is adjustable. Controls 80 are provided to enable the operator to either display all the echoes received or, as more commonly required, only the first echo.

The ramp voltage (vt) which deflects the oscilloscope beam away from the transducer arm is generated by the side range ramp circuit 68. When the transducer is pulsed, the 0.4837 megahertz clock from the control board 66 is applied to a ten bit binary storage register (the ramp register) which begins accumulating the count. The outputs of the ramp register are applied to a digital-to-analog converter which translates the digital outputs to an analog signal voltage; a ramp voltage then increases linearly with time to a value corresponding to about 100 inches. At this point, the register is reset, and when the next transducer is pulsed the register again commences through its counting sequence.

The side ranging transducers 78 are not located on the central line of the transducer arm, but are displaced about half the diameter of the arm. Similarly, the end ranging transducer is not located at the same r distance as transducers $L_{10}$ and $R_{10}$. Consequently, the ramp voltage, if it is to properly track the acoustic pulse away from the arm, must start at some distance from a point corresponding to the central line of the scanning arm in the case of the side ranging transducers. Also, the starting point of the ramp for the end ranging transducer must be displaced. The starting point displacements or offsets are established by presetting the ramp register to a digital number that corresponds to the proper offsets.

If, for example, the effective diameter (the distance between the diametrically opposed transducers) of the arm is 5.8 inches, then the required offset is 2.9 inches. The ramp counter must be preset to the number $2.9 \times 10 = 29$ or $(011101)_2$. The preset is established by six bit DIP switches located in the ramp circuits; one set for the side range transducers and one set for the end range transducer. At the end of each ramp the corresponding DIP switches preset the ramp counters to the proper starting point for the next ramp.

The ramp circuit also performs the pulse and receive decoder functions for the end ranging transducer. Outputs $Q_A$, $Q_B$ of the control circuit are decoded for this purpose.

Another function of the ramp board is the generation or control of the unblank signals which intensity modulate the display oscilloscope. Two outputs are provided. One output, the Z output, is intended for use with the X and Y outputs of the analog circuit previously described to generate a stored image display. A control is provided to allow the operator to display the transducer arm position on the stored image if desired. Another output, the UNMAG OUT, can be used with the UNMAG X and the UNMAG Y outputs to generate a real time image.

The dual pulser circuit 72 includes two complete pulser units in a single circuit arrangement. Each circuit is comprised of an input pulse shaping network and a high voltage switch. When an input pulse is received from the pulse decoder, the high voltage switch fires, generating a negative spike pulse which has a 10 nanosecond nominal rise time that is applied to the transducer. The amplitude of this spike pulse can be varied from 0 to about 250 volts by adjusting the high voltage applied to the dual pulser board.

Two separate receiver amplifiers make up the dual receiver circuit 74. The gain of the amplifier with a 50 ohm output load is nominally 250 and is adjustable in two 20 db steps with input attenuattor switches provided in the circuit. A continuous gain adjustment is provided by a 50 ohm input potentiometer. The amplifier input impedance is 50 ohms, and the bandwidth is nominally 18 megahertz. Since the transducers are operated in the pulse/echo mode, the negative high voltage spike from the pulser can be communicated to the receiver input. Therefore, the receiver inputs are protected by a diode clipper circuit.

Thus an effective ultrasonic imaging system is provided which presents the information in a format that allows easy interpretation by an operator. Reflections or echoes from one or more ultrasonic transducers are presented on a display so that a reflection from an object always occurs at the same place in the projection regardless of the position of the transducer receiving a back reflected signal. Thus, a complete map of objects viewed by the ranging transducers can be presented in a accurate intelligible format.

I claim:

1. An acoustic imaging system for displaying a viewed object comprising:
   a laterally extending array of a plurality of acoustic transducers respectively spaced at a known distance from a given point and directed to transmit and receive acoustic signals along preestablished transmission paths substantially parallel to a preselected plane;
   means for pivoting the array within the preselected plane about the given point;
   means for activating the transducers along the array to transmit and receive acoustic signals;
   means for generating output voltages for each respective reception of an acoustic signal corresponding to the coordinate position of the object viewed as the array is pivoted; and
   means for presenting the reception of each transducer on the same display at its corresponding coordinate position.

2. The imaging system of claim 1 wherein the means for activating the transducers sequentially activates the transducers along the array to transmit and receive acoustic signals.

3. The imaging system of claim 1 including means for pivoting the array within a given plane substantially perpendicular to the preselected plane.

4. The imaging system of claim 1 wherein the transducers are spaced from the pivot point.

5. The imaging system of claim 1 wherein the transducers are equally spaced along the lateral extension of the array.

6. The imaging system of claim 1 wherein the means for generating output voltages establishes the coordinate position of the viewed object from the time of flight of the reception, the distance from the pivot point of the transducer receiving the signal and the corresponding angle of rotation about the pivot of the receiving transducer.

7. The imaging system of claim 1 wherein the transducers are directed to transmit and receive acoustic signals along substantially parallel transmission paths.

* * * * *